(12) United States Patent
Mukkamala et al.

(10) Patent No.: US 6,727,387 B2
(45) Date of Patent: Apr. 27, 2004

(54) QUATERNARY AMMONIUM SALTS HAVING A TERTIARY ALKYL GROUP

(75) Inventors: Ravindranath Mukkamala, Houston, TX (US); Rajiv Monohar Banavali, Huntingdon Valley, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 10/139,440

(22) Filed: May 6, 2002

(65) Prior Publication Data

US 2003/0013769 A1 Jan. 16, 2003

Related U.S. Application Data

(60) Provisional application No. 60/290,904, filed on May 16, 2001.

(51) Int. Cl.$^7$ .............................................. A61K 31/14
(52) U.S. Cl. .................. 564/291; 564/292; 564/293; 564/294; 514/642; 254/390
(58) Field of Search ........................... 564/291, 292, 564/293, 294; 514/642; 254/390

(56) References Cited

U.S. PATENT DOCUMENTS

| | | |
|---|---|---|
| 3,219,639 A | 11/1965 | Fuchs et al. |
| 3,486,866 A | 12/1969 | Stromberg et al. |
| 3,910,971 A | 10/1975 | Hunsucker |
| 3,969,415 A | 7/1976 | Galantay |
| 4,022,909 A | 5/1977 | Hunsucker |
| 4,166,846 A | 9/1979 | Shigematsu et al. |
| 4,395,410 A | 7/1983 | Molloy et al. |

OTHER PUBLICATIONS

Database CAPLUS on STN, Acc. No. 1972:153508, Zhurnal Prikladnoi Khimii (Sankt–Peterburg, Russian Federation), (1972), 45(2), p. 439–43 (abstract).*

Zhurnal Prikladnoi Khimii (Sankt–Peterburg, Russian Federation), (1972), 45(2), p. 439–43 (English translation).*

Manning P. Cooke, Jr. et al., J. Org. Chem., Reduction of Quaternary Ammonium Salts with Lithium Triethylborohydride. A Convenient Method for the Demethylation of Substituted Trimethylammonium Salts, vol. 40, No. 4, pp. 531–532 (1975).

Peter Nussbaumer et al., J. Med. Chem., Synthesis and Structure–Activity Relationships of Side–Chain–Substituted Analogs of the Allylamine Antimycotic Terbinafine Lacking the Central Amino Function. vol. 38, No. 10, pp. 1831–1836 (1995).

F. M. Menger et al., J. Am. Chem. Soc., A Microscopic Hydrophobicity Parameter. vol. 108, No. 11, pp. 2980–2984 (1986).

* cited by examiner

*Primary Examiner*—Brian Davis
(74) *Attorney, Agent, or Firm*—Kenneth Crimaldi

(57) ABSTRACT

A compound of formula I:

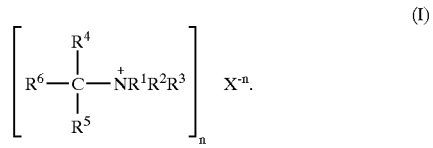

16 Claims, No Drawings

QUATERNARY AMMONIUM SALTS HAVING A TERTIARY ALKYL GROUP

CROSS REFERENCE TO RELATED PATENT APPLICATIONS

This is a non-provisional application of prior pending U.S. provisional application Ser. No. 60/290,904 filed May 16, 2001.

BACKGROUND

This invention relates to novel quaternary ammonium salts useful in several applications, including phase-transfer catalysis, corrosion inhibition, inhibition of microbial growth, and development of antistatic agents.

Quaternary ammonium salts in which one of the groups attached to nitrogen is a tertiary alkyl group are known in the literature only for relatively small alkyl groups such as t-butyl or t-octyl. The quaternary salt formed from 1,1,3,3-tetramethylbutanamine is described in Journal of Organic Chemistry, vol. 40, pp. 531–2 (1975).

The problem addressed by this invention is to provide quaternary ammonium salts containing large branched alkyl groups, and methods for use of these salts as biocides, corrosion inhibitors and phase transfer catalysts.

STATEMENT OF INVENTION

This invention is directed to a compound of formula I:

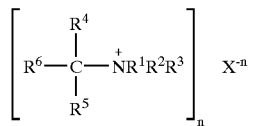

wherein $R^1$ is $C_1-C_{18}$ alkyl, $C_1-C_{18}$ polyether alkyl, $C_1-C_{18}$ alkenyl, $C_1-C_{18}$ alkynyl, or $C_7-C_{12}$ aralkyl; $R^2$ is $C_1-C_4$ alkyl; $R^3$ is methyl or ethyl; $R^4$, $R^5$ and $R^6$ are independently $C_1-C_{21}$ alkyl, substituted $C_1-C_{21}$ alkyl, $C_1-C_{21}$ alkenyl or substituted $C_1-C_{21}$ alkenyl; $X^{-n}$ is halide, hydroxide, tetrafluoroborate, phosphate or an organic anion having from 1 to 20 carbon atoms; and n is an integer from 1 to 5;
  wherein at least one of $R^4$, $R^5$ and $R^6$ is branched;
  and wherein $R^4$, $R^5$ and $R^6$ contain collectively at least nine carbon atoms.

DETAILED DESCRIPTION

An "alkyl" group is a saturated hydrocarbyl group having from one to twenty-one carbon atoms in a linear, branched or cyclic arrangement. A "polyether alkyl" group is an alkyl group comprising an oligomer of an alkyl epoxide, e.g., ethylene oxide or propylene oxide, where the oligomer optionally is end-capped with an alkyl or alkenyl group. An "alkenyl" group is an "alkyl" group in which at least one carbon-carbon single bond has been replaced with a double bond. Substituted alkyl and alkenyl groups are substituted with one or more hydroxy; halo; cyano; alkyl; alkoxy; carbalkoxy; carboxy; amino; alkylamino; or nitro groups, with substitution by one or more halo groups being possible on alkyl or alkoxy groups. An "alkynyl" group is an "alkyl" group in which at least one carbon-carbon single bond has been replaced with a triple bond. Preferably, alkyl, alkenyl and alkynyl groups are acyclic and unsubstituted. An "aryl" group is a substituent derived from an aromatic hydrocarbon compound. An aryl group has a total of from six to twenty ring atoms, and has one or more rings which are separate or fused. Substitution on aryl groups of one or more hydroxy; halo; cyano; alkoxy; alkyl; alkenyl; carbalkoxy; carboxy; or nitro groups is permitted, with substitution by one or more halo groups being possible on alkyl, alkenyl or alkoxy groups. An "aralkyl" group is an "alkyl" group substituted by an "aryl" group.

$X^{-n}$ is halide, hydroxide, tetrafluoroborate, phosphate, or an organic anion having from 1 to 20 carbon atoms. Organic anions are those containing carbon, with the exception of carbonate, bicarbonate, cyanide, cyanate and thiocyanate, preferably those containing carbon and hydrogen, including, for example, phosphonates, alkoxides, carboxylates, hydrocarbyl sulfates and sulfonates, and chelating carboxylic acids. $X^{-n}$ is the conjugate base of an acid $H_mX$, having m acidic hydrogen atoms, where $m \geq n$. Preferably, m is no greater than 10. Preferably, the pKa for removal of the most acidic hydrogen atom in the acid $H_mX$ is no greater than 17; more preferably the pKa for removal of the most acidic hydrogen atom in $H_mX$ is no greater than 9. Preferably, $X^{-n}$ is selected from the group consisting of halide; hydroxide; alkoxide; alkyl, aryl, aralkyl, alkenyl, and alkylamino carboxylates; alkyl and aryl sulfates; alkyl and aryl sulfonates; phosphates; phosphonates; alkyl, aryl, aralkyl, alkenyl, and alkylamino thiocarboxylates; chelating aliphatic carboxylic acids; and tetrafluoroborate. More preferably, $X^{-n}$ is selected from the group consisting of halide, alkyl sulfate, aliphatic phosphonate and chelating aliphatic carboxylic acids. Particularly preferred aliphatic phosphonates are the anions derived from aminotrimethylenephosphonic acid (ATMP), diethylenetriamine pentamethylenephosphonic acid (DETA), bis-hexamethylenetriamine-pentaphosphonic acid (BHMT) and hydroxyethylidene diphosphonic acid (HEDP). Particularly preferred chelating carboxylic acids include ethylenediaminetetraacetic acid (EDTA) and nitrilotriacetic acid.

For multivalent acids $H_mX$, e.g., the aforementioned phosphonates, the conjugate base $X^{-n}$ can have n equal to 1, 2, 3, 4 or 5, up to the number of acidic hydrogen atoms m in the acid $H_mX$. When the conjugate base is formed by neutralization of the acid $H_mX$, the number of equivalents of base used to form the conjugate base will determine the value of n. To maintain charge balance, the number of quaternary ammonium ions in the compound will be equal to n. In a preferred embodiment of the invention, n is 1, i.e., $X^{-n}$ is $X^-$. Preferably, $X^-$ is halide or alkyl sulfate, most preferably iodide or bromide.

Preferably, the quaternary salts of formula I are prepared from tertiary-alkyl primary or secondary amines. Preferably, $R^4$, $R^5$ and $R^6$ in formula I all are alkyl groups. Preferably, formula I represents a mixture of compounds among which there are differences in the alkyl groups $R^4$, $R^5$ and $R^6$. Particularly preferred mixtures of tertiary-alkyl primary or secondary amines are Primene® BC-9 amine, Primene® 81-R amine, Primene® JM-T amine, or Primene® LA-2 amine, all of which are available from Rohm and Haas Company, Philadelphia, Pa. In each of the first three of these, which are tertiary-alkyl primary amines, the $R^4R^5R^6C$— unit is a mixture of $C_9-C_{10}$, $C_{10}-C_{15}$, $C_{16}-C_{22}$ hydrocarbons, respectively. Primene® LA-2 amine is derived from Primene® 81-R amine by alkylation of the amine with a single n-$C_{12}$ alkyl group. In each of the Primene® amines, at least one of the $R^4$, $R^5$ and $R^6$ groups is branched. Preferably, $R^1$ is a $C_1-C_{12}$ alkyl group.

In one embodiment of the invention, $R^4$, $R^5$ and $R^6$ all are alkyl. Preferably, $R^2$ and $R^3$ are methyl and $X^-$ is halide, phosphonate or a chelating carboxylic acid. More preferably, $R^1$, $R^2$ and $R^3$ all are methyl and $X^-$ is bromide or iodide. Preferably, $R^4$, $R^5$ and $R^6$ contain collectively at least ten carbon atoms. More preferably, $R^4$, $R^5$ and $R^6$ contain collectively at least twelve carbon atoms.

The present invention is further directed to a method for inhibiting the growth of microorganisms, including, but not limited to bacteria, fungi, algae and yeasts, by introducing a microbicidally effective amount of the compound to a locus that is subject to microbial attack. The amount of compound to be used depends on the application. Typically the amount of compound of Formula I incorporated into a locus is from 0.1 to 10,000 ppm, preferably from 0.5 to 5,000 ppm and more preferably from 1 to 1000 ppm.

Suitable loci include, for example: cooling towers; air washers; boilers; mineral slurries; wastewater treatment; ornamental fountains; marine structures, such as boats, ships, oil platforms, piers, pilings, docks, elastomeric rubbers and fish nets; marine antifouling coatings, such as marine paints and varnishes; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; crude oil; oilfield fluids, such as injection water, fracture fluids, and drilling muds; agriculture adjuvant preservation; surfactant preservation; medical devices; contact lenses; diagnostic reagent preservation; food preservation, such as plastic or paper food wrap; and pools and spas.

Preferably, the antimicrobial compounds of the present invention are used to inhibit the growth of microorganisms at a locus selected from petroleum processing fluids; fuel; crude oil; oilfield fluids, such as injection water, fracture fluids, and drilling muds; cooling towers, mineral slurries, pulp and paper processing fluids, plastics, emulsions, dispersions, paints, latexes, coatings, construction products, marine structures, household products, cosmetics, toiletries, shampoos, soaps, detergents, industrial cleaners, metalworking fluids, textiles and textile products, wood and wood products, surfactants and diagnostic reagents.

Optionally, the compounds of Formula I can be used in combination with other microbicidal compounds. Formulated compositions comprising an effective amount of a compound of Formula I with an acceptable carrier may be used or the compounds may be applied directly to the end-use environment.

The present invention is further directed to a method for performing reactions with phase transfer catalysis by the compound of formula I, i.e., performing heterogeneous ionic reactions in a two-phase reaction system containing an organic phase and an aqueous phase in the presence of a compound of formula I.

The present invention is further directed to a method for inhibiting corrosion of metals by incorporation of a compound of formula I into a fluid in contact with a metal. Preferably, the metal is steel or copper. Preferably, the concentration of the compound of formula I in the fluid is from 100 ppm to 5%.

The present invention is further directed to a method for extracting metal ions from an aqueous phase into an organic phase by contacting a metal-containing aqueous phase, an organic phase and at least one compound of formula I. Preferred metals include, for example, alkali and alkaline earth metals, gold, cadmium, cobalt, iron, molybdenum, rare earth metals, tungsten, uranium, vanadium and zinc.

The present invention is further directed to a method for decreasing the undesirable effects resulting from the presence of a static charge on a surface by treating the surface with a compound of formula I.

In one embodiment of the invention, the compounds of formula I are prepared by treating the corresponding tertiary-alkyl primary or secondary amine with an excess of an alkylating agent, $R^3X$, for example, an alkyl halide in the presence of a base. Useful bases include sodium and potassium hydroxide, although those skilled in the art will recognize that other bases are suitable. Typically, the reaction is performed in a two-phase mixture of the tertiary-alkyl primary or secondary amine and an aqueous base solution, although it is also possible to perform the reaction in a single-phase solvent or solvent mixture. This method will be referred to as "Route A."

In another embodiment of the invention, the compounds of formula I are prepared in two steps: alkylating a tertiary-alkyl primary or secondary amine to form a tertiary amine, and then treating the tertiary amine with an excess of an alkylating agent, for example, an alkyl halide. The initial alkylation of the tertiary-alkyl primary or secondary amine is performed by any standard alkylation procedure known to be suitable for this purpose, for example, methylation with formaldehyde and formic acid. The subsequent reaction with an alkylating agent does not require the presence of a base, and typically would be performed in a one-phase organic solvent system. This method will be referred to as "Route B."

In one embodiment of the invention, the anion $X^-$ which is derived from the alkylating agent, $R^3X$, is replaced with another anion $X^-$ by means of an ion exchange process.

Preferably, the alkylating agent, $R^3X$, used to prepare the quaternary salt is a methylating agent or an ethylating agent in which $R^3$ is methyl or ethyl, and X is halo, alkyl sulfate, tosylate, triflate or mesylate. Most preferably, the alkylating agent is methyl iodide or methyl bromide.

When the groups $R^1$, $R^2$ and $R^3$ all are methyl, the product is a tertiary-alkyl trimethylammonium salt. This salt is prepared either by Route A or Route B. Route A for this salt is illustrated by the following scheme:

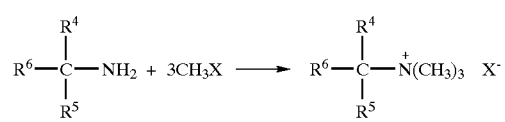

This process typically is carried out in the presence of two equivalents of base to neutralize the HX produced by the reaction. Route B for this salt is illustrated by the following scheme:

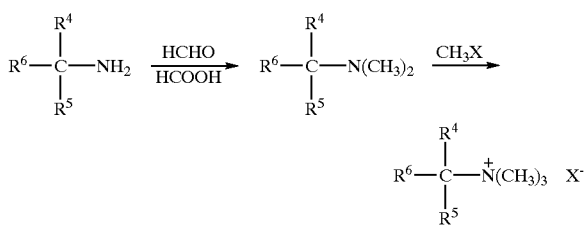

EXAMPLES

N,N,N-Trimethyl t-octyl ammonium iodide: To a stirred mixture of neat t-octylamine (12.9 g, 100 mmol) was added methyl iodide (42.5 g, 300 mmol) drop-wise. The reaction mixture became quite hot, and a thick paste-like material resulted. After cooling the mixture in a cool water bath, a solution of sodium hydroxide (24 g, 600 mmol, in 100 mL water) was added while the solid-paste was being mixed with a glass rod. Then the mixture was heated under reflux for 5 h, then chilled in an ice bath. The obtained solid was filtered, washed with some cold water, and suction dried. It was then recrystallized from 5 wt % sodium hydroxide solution at 5° C. to get a white crystalline material that was filtered, and suction-dried overnight (4.5 g, 15%); mp: 266° C. (by DSC). $^1$H NMR (CDCl$_3$): δ3.33 (s, 9H, —N$^+$(CH$_3$)$_3$), 1.83 (s, 2H, —CH$_2$—), 1.62 (bs, 6H, —C(CH$_3$)$_2$—), 1.12 (s, 9H, —C(CH$_3$)$_3$) ppm.

N,N,N-Trimethyl 81-R ammonium iodide: The procedure given in the previous example was followed. Starting from Primene® 81-R amine (18.5 g, 100 mmol), methyl iodide (56.7 g, 400 mmol), and NaOH (24 g, 600 mmol), product was obtained as light yellow waxy solid (2.6 g, 7%). $^1$H NMR (CDCl$_3$): δ3.36 (ms, 9H, —N$^+$(CH$_3$)$_3$), 2.5–2.1 (m, 3.2H, —N—CH$_3$), 1.9–0.7 (m, ca.40H, alkyl portion of 81-R) ppm.

N,N,N-Trimethyl n-octyl ammonium iodide: To well stirred mixture of n-octyl amine (12.9 g, 100 mmol), and aqueous sodium hydroxide solution (24 g, 600 mmol, in 100 mL water), added drop-wise neat methyl iodide (57 g, 400 mmol), while the reaction mixture was cooled in a water bath. After the addition was complete, the mixture was heated under reflux for 5 h, and the product isolated as in the procedure given in the first example. Recrystallization from water gave white crystalline solid (16.1 g, 54%). $^1$H NMR (CDCl$_3$): δ3.5 (bt, 2H, 3.33, —N$^+$CH$_2$—), 3.3 (s, 9H, —N$^+$(CH$_3$)$_3$), 1.7 and 1.2 (bs, 12H, (—CH$_2$—)$_6$), 0.8 (bt, 3H, —CH$_3$) ppm.

N,N,N-Trimethyl JM-T ammonium iodide: The procedure given in the previous example was followed. Primene® JM-T amine (26.9 g, 100 mmol), methyl iodide (57.8, 400 mmol), and NaOH (24 g, 600 mmol) were used. After the reflux, two organic layers were separated. The top layer did not contain any quaternary salts as determined from the NMR. The bottom organic layer was mixed with 100 mL of toluene, the water layer separated from it, dried with anhydrous sodium sulfate, and the solvent evaporated to obtain a yellow solid. This solid was further dissolved in 100 mL chloroform, filtered to remove some insoluble solid, and once again, solvent was evaporated to get a sticky, dark-yellow solid (6.4 g, 15%). $^1$H NMR (CDCl$_3$): δ3.5 (bm, 9H, —N$^+$(CH$_3$)$_3$), 2.3 (m, ca. 4H, —N(CH$_3$)$_2$), 2.1–0.7 (bm, ca. 68H, alkyl portion of JM-T) ppm.

N,N-Dimethyl t-octylamine: To a mixture of formic acid (27.6 g, 600 mmol) and paraformaldehyde (12 g, 400 mmol) was added drop-wise t-octyl amine while being heated between 50–60° C. After the addition was complete, the mixture was heated at 80–90° C. for ca. 30 min during which time, release of a lot of gas as bubbles was observed. The mixture was cooled to 5° C. and then neutralized with sodium hydroxide solution (12 g in 40 mL water) while the temperature was being maintained below 15° C. The dark amber colored organic layer was separated from the mixture, and purified by distillation under atmospheric pressure to give a colorless liquid (20.2 g, 64%); bp. 160–170° C. $^1$H NMR (CDCl$_3$): δ2.21 (s, 6H, —N(CH$_3$)$_2$), 1.39 (s, 2H, —CH$_2$—), 1.11 (s, 6H, —C(CH$_3$)$_2$—), 1.0 (s, 9H, —C(CH$_3$)$_3$) ppm; IR (Neat): 2952, 2818, 2777, 1463, 1380 cm$^{-1}$.

N,N-Dimethyl 81-R: The procedure given in the previous example was followed. Starting from Primene® 81-R amine (35.5 g, ca. 200 mmol), formic acid (30 g, 652 mmol), and paraformaldehyde (13.5 g, 450 mmol) crude product was obtained as an amber-yellow liquid. Purified by vacuum distillation (bp. 80–100° C. at 0.1 mm Hg) afforded clear light yellow liquid (37 g, 87%). $^1$H NMR (CDCl$_3$): δ2.5–2.1 (m, 6H, —N(CH$_3$)$_2$), 1.9–0.7 (m, 34H, alkyl proton of 81-R) ppm; IR (Neat): 2958, 2872, 2820, 2779, 1463, 1378 cm$^{-1}$.

N,N-Dimethyl JM-T: The procedure given in the previous example was followed. Starting from Primene® JM-T amine (53.8 g, ca.200 mmol), formic acid (30 g, 652 mmol), and paraformaldehyde (13.5 g, 450 mmol) crude product was obtained as thick amber liquid. Purified by vacuum distillation (bp.105–135° C. at 0.1 mm Hg) afforded clear light yellow liquid (37 g, 66%). $^1$H NMR (CDCl$_3$): δ2.5–2.1 (m, 6H, —N(CH$_3$)$_2$), 1.9–0.6 (m, 44H, alkyl proton of JM-T) ppm; IR (Neat): 2958, 2872, 2819, 2779, 1463, 1378 cm$^{-1}$.

N-Methyl Amberlite® LA-2: The procedure given in the previous example was followed. Starting from Amberlite® LA-2 amine (59.3 g, ca.150 mmol), formic acid (41.4 g, 900 mmol), and paraformaldehyde (15.7 g, 525 mmol), crude product was obtained as dark amber liquid, which appeared to contain some water emulsion. Purification was attempted by vacuum distillation; about 10–15% of low boiling impurities were distilled between 80–120° C. at 0.1 mm Hg), but the main product did not distill even up to 200° C. (oil bath). The liquid which remained undistilled (47.5 g, 75%) was used further without any further purification. $^1$H NMR (CDCl$_3$): δ2.5–2.1 (m, 5H, —CH$_2$—N(CH$_3$)), 1.5–1.2, and 1.0–0.8 (two m, ca. 51H, alkyl proton of LA-2) ppm.

N,N,N-Trimethyl t-octylammonium iodide: To a stirred and cooled (water bath) solution of N,N-dimethyl t-octylamine (5 g, 31.8 mmol) in dichloromethane (30 mL) was added methyl iodide (6.7 g, 47.7 mmol) drop-wise. A slight increase in temperature was observed along with the formation light yellow precipitate. Stirring was continued for 24 h at room temperature, and at the end of this period, the solvent and excess methyl iodide were evaporated to produce a light yellow powder. This solid was washed with excess of n-pentane (3×75 mL), filtered, and suction dried (9.0 g, 95%). mp: ca. 260° C. (by DSC). $^1$H NMR (CDCl$_3$): δ3.33 (s, 9H, —N$^+$(CH$_3$)$_3$), 1.82 (s, 2H, —CH$_2$—), 1.61 (bt, 6H, —C(CH$_3$)$_2$—), 1.12 (s, 9H, —C(CH$_3$)$_3$) ppm.

N,N,N-Trimethyl t-octyl ammonium bromide: The procedure given in the previous example was followed. Starting with a solution of N,N-dimethyl t-octylamine (5 g, 31.8 mmol) in dichloromethane (5 mL) and methyl bromide (2.0 M solution in t-butyl methyl ether, 42.8 mL, 85.6 mmol), product was obtained as a white solid (7.2 g (90%)). $^1$H NMR (CDCl$_3$): δ3.35 (s, 9H, —N$^+$(CH$_3$)$_3$), 1.79 (s, 2H, —CH$_2$—), 1.60 (bt, 6H, —C(CH$_3$)$_2$—), 1.11 (s, 9H, —C(CH$_3$)$_3$) ppm.

N,N,N-Trimethyl 81-R ammonium iodide: The procedure given in the previous example was followed, starting with N,N-dimethyl Primene® 81-R amine (10 g, ca. 47 mmol), and methyl iodide (13.3 g, 94 mmol), and dichloromethane (15 mL). The reaction mixture was stirred at room temperature for 40 h. The solid obtained after solvent evaporation was dissolved in chloroform (100 mL), and insoluble solid was filtered off. Solvent evaporation gave a sticky yellow solid that was washed with an excess of n-pentane (3×80 mL), and decanted. The remaining solvent was evaporated under vacuum to get a reasonably dry yellow solid (8.3 g, 50%). $^1$H NMR (CDCl$_3$): δ3.4 (ms, 9H, —N$^+$(CH$_3$)$_3$), 2.9 (bm, 2.8 H, —HN$^+$(CH$_3$)$_2$), 2.1–0.7 (m, ca. 44 H, alkyl portion of 81-R) ppm.

N,N,N-Trimethyl JM-T ammonium iodide: The procedure given in the previous example was followed, but the reaction time was 3 days.

Starting with N,N-dimethyl Primene® JM-T amine (7.5 g, ca. 25 mmol) in 5 mL chloroform, and methyl iodide (17.2 g, 100 mmol), a yellow viscous solid-liquid was obtained as crude product. It was dissolved in 100 mL chloroform, filtered to remove the insoluble solid, and the solvent evaporated to give a dirty-mustard-colored sticky solid (7.8 g, 71%). $^1$H NMR (CDCl$_3$): δ3.4 (m, 9H, —N$^+$(CH$_3$)$_3$), 2.8 (m, ca. 6H, —N$^+$H(CH$_3$)$_2$), 2.1–0.7 (bm, ca. 135 H, alkyl portion of JM-T) ppm.

N,N-Dimethyl LA-2 ammonium iodide: A solution of N-methyl Primene® LA-2 amine (7.0 g, ca. 16 mmol), 5 mL chloroform, and methyl iodide (6.8 g, 47.9 mmol) was stirred at room temperature and the progress of the reaction was followed by proton NMR spectroscopy. After 3 days, a quaternary ammonium salt was formed in only about 15% yield. The stirring was continued for a total of 14 days, and during this time, the amount of quaternary salt in the reaction mixture was raised to ca. 66%. More chloroform (100 mL) was added to the reaction mixture and the solution was filtered to remove any insoluble by-products (none were observed). Evaporation of the solvent gave a dirty-mustard-colored liquid (9.4 g, 100%) which had two layers that were separated by means of a separatory funnel; some of the liquid (ca. 1 g) was lost in this operation as it got stuck to the funnel. Proton NMR analysis indicated that top layer (ca. 1 g) contained no quaternary salt, and contained only the unreacted starting material. The bottom layer (7.4 g, 78%) soon turned into a sticky solid, and was found to be a mixture of 66% quaternary salt and 34% of starting material. $^1$H NMR (CDCl$_3$): δ3.6–3.1 (m, 8H, —N$^+$(CH$_3$)$_2$CH$_2$—), 2.8–2.3 (broad hump, ca. 4H, —N$^+$H(CH$_3$)$_2$), 2.1–0.6 (bm, ca. 88 H, alkyl portion of LA-2) ppm.

Yields and product distributions for quaternary salts derived from several tertiary-alkyl primary amines are summarized in Table 1 below. Primene® 81-R amine is indicated by "81-R," Primene® JM-T amine by "JM-T," and Primene® LA-2 amine by "LA-2." Products derived from tertiary-octylamine (1-amino-1,1,3,3-tetramethylbutane; "TOA") are included for comparison, although these are not within the scope of the present invention.

TABLE 1

Yields and product distributions in quaternary salt synthesis.

| amine/ alkyl halide | Route A | | | | Route B | | | |
|---|---|---|---|---|---|---|---|---|
| | Yield[a] | Product Distribution[b] | | | Yield[a] | Product Distribution[b] | | |
| | | Quat | 2°/3° amines | 1° | | Quat | 2° salt | olefin |
| TOA/MeI | 15 | 100 | — | — | 94 | 100 | — | — |
| TOA/MeBr | — | — | — | — | 90 | 100 | — | — |
| 81-R/MeI | 7 | 66 | 23 | 11 | 50 | 62 | 29 | 10 |
| JM-T/MeI | 15 | 53 | 36 | 11[c] | 71 | 28 | 28 | 44[c] |
| LA-2/MeI | — | — | — | — | 85 | 60 | 40[d] | — |

[a]Isolated yield; note that in the case of 81-R, JM-T and LA-2, this represents the yield of the total product mixture and not that of the quat alone.
[b]Determined by proton NMR peak integrations (±10%).
[c]Along with the olefin contaminant present in the starting JM-T.
[d]Not a 2° salt - unreacted methyl LA-2.

The five alkylation products from Route B, as described in Table 1, were tested for their ability to inhibit the growth of a Gram-positive bacterium, Staphylococcus aureus 6538 and a Gram-negative bacterium, Pseudomonas aeruginosa 13388 in a high resolution minimum inhibitory concentration (HRMIC) test. Two of the compounds showing biological activity were also tested for activity against sulfate-reducing bacteria (SRB). The details of various tests and results are given below.

HR MIC Test Method: Varying amounts of test compound dissolved in DMSO were added to M9GY in a 96-well microtiter plate. Ten-fold serial dilutions were performed on a Biomek 2000 Workstation to obtain a range of closely spaced concentrations of biocide as illustrated in Table 2. A cell suspension of either Pseudomonas aeruginosa 13388 or Staphylococcus aureus 6538, adjusted to provide 10$^6$ CFU/ml in each well, was added to each microtiter plate. Kathon® WT biocide and Hyamine® 3500 biocide (dimethyl benzyl ammonium chloride) were included in the test for comparison. The microtiter plates were incubated at 30° C. for 24 hours and were then checked for the presence or absence of microbial growth in each well. The concentration of biocide in the first microtiter well demonstrating no growth was the Minimum Inhibitory Concentration (MIC) for the biocide. Each compound was evaluated in duplicate on three separate days.

TABLE 2

Biocide concentration (ppm active ingredient) in a typical HRMIC test

| | 1 | 2 | 3 | 4 | 5 | 6 | 7 | 8 | 9 | 10 | 11 | 12 |
|---|---|---|---|---|---|---|---|---|---|---|---|---|
| A | 1000 | 100 | 10 | 1 | 0.1 | 0 | 1000 | 100 | 10 | 1 | 0.1 | 0 |
| B | 800 | 80 | 8 | 0.8 | 0.08 | 0 | 800 | 80 | 8 | 0.8 | 0.08 | 0 |

TABLE 2-continued

Biocide concentration (ppm active ingredient) in a typical HRMIC test

|   | 1 | 2 | 3 | 4 | 5 | 6 | 7 | 8 | 9 | 10 | 11 | 12 |
|---|---|---|---|---|---|---|---|---|---|----|----|----|
| C | 700 | 70 | 7 | 0.7 | 0.07 | 0 | 700 | 70 | 7 | 0.7 | 0.07 | 0 |
| D | 600 | 60 | 6 | 0.6 | 0.06 | 0 | 600 | 60 | 6 | 0.6 | 0.06 | 0 |
| E | 500 | 50 | 5 | 0.5 | 0.05 | 0 | 500 | 50 | 5 | 0.5 | 0.05 | 0 |
| F | 400 | 40 | 4 | 0.4 | 0.04 | 0 | 400 | 40 | 4 | 0.4 | 0.04 | 0 |
| G | 300 | 30 | 3 | 0.3 | 0.03 | 0 | 300 | 30 | 3 | 0.3 | 0.03 | 0 |
| H | 200 | 20 | 2 | 0.2 | 0.02 | 0 | 200 | 20 | 2 | 0.2 | 0.02 | 0 |

SRB MIC Test Method: Varying amounts of test compounds were dissolved in DMSO and added to modified Sulfate API Broth in sterile vials. This media was modified to remove reducing agents but treated in such a way as to minimize oxygen content. Two-fold serial dilutions were performed in an anaerobic chamber to obtain a range of closely spaced concentrations of test compound ("TC") as illustrated in Table 3. A cell suspension of the sulfate reducing bacteria *Desulfovibrio desulfuricans* ATCC 7757 was added to provide $10^6$ CFU/mL in each vial. Kathon® WT biocide and Primene® 81-R amine were included in the test for comparison. The vials were incubated at 35° C. for 3 days and were then checked for the presence or absence of microbial growth as indicated by a black precipitate formed by reduction of sulfate to hydrogen sulfide by the bacteria. The lowest concentration of compound that inhibited growth of the test organism was the Minimum Inhibitory Concentration (MIC) for the compound.

TABLE 3

Biocide concentration in SRB MIC test

| TC | 1 | 2 | 3 | 4 | 5 | 6 | 7 | 8 | 9 | 10 |
|----|---|---|---|---|---|---|---|---|---|----|
| I  | 1000 | 500 | 250 | 125 | 62.5 | 31.3 | 15.6 | 7.8 | 3.9 | 2.0 |
|    | 900 | 450 | 225 | 112.5 | 56.3 | 28.1 | 14.1 | 7.0 | 3.5 | 1.8 |
|    | 800 | 400 | 200 | 100 | 50 | 25 | 12.5 | 6.3 | 3.1 | 1.6 |
| II[a] | 10 | 5 | 2.5 | 1.3 | 0.6 | 0.3 | | | | |
|    | 8 | 4 | 2.0 | 1.0 | 0.5 | 0.25 | | | | |

[a]Kathon ® WT, 1.5%

HR MIC Test Results: Alkylation products derived from JM-T and LA-2 ("JM-T-Q" and "LA-2-Q" respectively) showed activity against both Gram-negative and Gram-positive test organisms. The MIC of the latter was comparable to that of Hyamine® 3500 biocide (dimethyl benzyl ammonium chloride) while the MIC of the former was about ten-fold higher. The alkylation product derived from 81-R ("81-R-Q") was only active against the Gram-positive bacteria and the MIC was three orders of magnitude higher than the MIC of Hyamine® 3500 biocide ("HB"). The previously described alkylation products derived from t-octyl amine (TOA I and TOA Br) showed no activity against either the Gram-positive or the Gram-negative bacteria in this test. Results from Kathon® EDC biocide ("KB") are also included. Results are presented in Table 4.

TABLE 4

Antimicrobial activity of Quaternary compounds versus Gram-positive and Gram-negative bacteria.

|    | Gram-positive[a] | | | Gram-negative[b] | | |
|----|---|---|---|---|---|---|
| TC | MIC (ppm) Average | N | Std. error | MIC (ppm) Average | N | Std. error |
| KB | 0.38 | 4 | 0.03 | 1.83 | 6 | 0.18 |
| HB | 0.18 | 4 | 0.03 | 17.5 | 4 | 2.89 |
| TOA I⁻ | >1000 | 2 | na | >1000 | 2 | na |
| TOA Br⁻ | >1000 | 2 | na | >1000 | 2 | na |
| 81-R-Q | 350 | 6 | 24.49 | >1000 | 2 | na |
| JM-T-Q | 2.0 | 6 | 0.28 | 200 | 6 | 0 |
| LA-2-Q | 0.40 | 6 | 0 | 40 | 6 | 0 |

[a]*Staphylococcus aureus* 6538
[b]*Pseudomonas aeruginosa* 13388

SRB MIC Test Results: Both LA-2-Q and JM-T-Q showed activity against the sulfate reducing bacteria. The activity of LA-2-Q was at least a magnitude better than the Primene® 81-R amine control and comparable to that of Kathon® biocide. The activity of JM-T-Q was comparable to that of the Primene® 81-R amine control (see Table 5).

TABLE 5

Antimicrobial Activity of Quaternary compounds versus Sulfate-Reducing Bacteria

| Test Compound | MIC (ppm active ingredient) |
|---|---|
| JM-T-Q | 200 |
| LA-2-Q | 15.6 |
| Primene ® 81-R amine | 225 |
| Kathon ® WT biocide | 8 |

What is claimed is:
1. A compound having the formula:

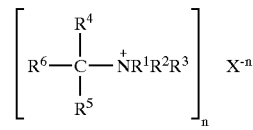

wherein $R^1$ is $C_1$–$C_{18}$ alkyl, $C_4$–$C_{18}$ polyether alkyl, $C_1$–$C_{18}$ alkenyl, $C_1$–$C_{18}$ alkynyl, or $C_7$–$C_{12}$ aralkyl; $R^2$ is $C_1$–$C_4$ alkyl; $R^3$ is methyl or ethyl; $R^4$, $R^5$ and $R^6$ are independently $C_1$–$C_{21}$ alkyl, or substituted $C_1$–$C_{21}$ alkyl; $X^{-n}$ is halide, hydroxide, tetrafluoroborate, phosphate or an organic anion having from 1 to 20 carbon atoms; and n is an integer from 1 to 5;
wherein at least one of $R^4$, $R^5$ and $R^6$ is branched;
and wherein $R^4$, $R^5$ and $R^6$ contain collectively at least nine carbon atoms.

2. The compound of claim 1 in which $R^4$, $R^5$ and $R^6$ are alkyl.

3. The compound of claim 2 in which $R^2$ and $R^3$ are methyl and $X^-$ is halide, phosphonate or a chelating carboxylic acid.

4. The compound of claim 3 in which $R^1$ is methyl and $X^-$ is bromide or iodide.

5. A method for inhibiting growth of microorganisms comprising introducing to a locus that is subject to microbial attack a microbicidally effective amount of a compound of formula:

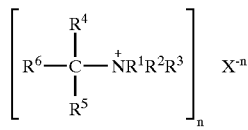

wherein $R^1$ is $C_1$–$C_{18}$ alkyl, $C_4$–$C_{18}$ polyether alkyl, $C_1$–$C_{18}$ alkenyl, $C_1$–$C_{18}$ alkynyl, or $C_7$–$C_{12}$ aralkyl; $R^2$ is $C_1$–$C_4$ alkyl; $R^3$ is methyl or ethyl; $R^4$, $R_5$ and $R_6$ are independently $C_1$–$C_{21}$ alkyl, or substituted $C_1$–$C_{21}$ alkyl, $C_1$–$C_{21}$ alkenyl or substituted $C_1$–$C_{21}$ alkenyl; $X^{-n}$ is halide, hydroxide, tetrafluoroborate, phosphate or an organic anion having from one to 20 carbon atoms; and n is an integer from 1 to 5;

wherein at least one of $R^4$, $R^5$ and $R^6$ is branched;

and wherein $R^4$, $R^5$ and $R^6$ contain collectively at least nine carbon atoms.

6. The method of claim 5 in which $R^4$, $R^5$ and $R^6$ are alkyl; and $R^1$, $R^2$ and $R^3$ are methyl.

7. A method for inhibiting corrosion of a metal comprising introducing to a material which contacts the metal an effective amount of a compound of formula:

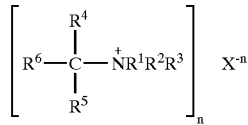

wherein $R^1$ is $C_1$–$C_{18}$ alkyl, $C_4$–$C_{18}$ polyether alkyl, $C_1$–$C_{18}$ alkenyl, $C_1$–$C_{18}$ alkynyl, or $C_7$–$C_{12}$ aralkyl; $R^2$ is $C_1$–$C_4$ alkyl; $R^3$ is methyl or ethyl; $R^4$, $R_5$ and $R^6$ are independently $C_1$–$C_{21}$ alkyl, or substituted $C_1$–$C_{21}$ alkyl; $X^{-n}$ is halide, hydroxide, tetrafluoroborate, phosphate or an organic anion having from 1 to 20 carbon atoms; and n is an integer from 1 to 5;

wherein at least one of $R^4$, $R^5$ and $R^6$ is branched;

and wherein $R^4$, $R^5$ and $R^6$ contain collectively at least nine carbon atoms.

8. A composition produced by allowing a compound of formula:

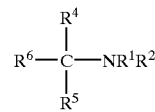

wherein $R^1$ is $C_1$–$C_{18}$ alkyl, $C_4$–$C_{18}$ polyether alkyl, $C_1$–$C_{18}$ alkenyl, $C_1$–$C_{18}$ alkynyl, or $C_7$–$C_{12}$ aralkyl; $R^2$ is $C_1$–$C_4$ alkyl; and $R^4$, $R^5$ and $R^6$ are independently $C_1$–$C_{21}$ alkyl, or substituted $C_1$–$C_{21}$ alkyl;

wherein at least one of $R^4$, $R^5$ and $R^6$ is branched;

and wherein $R^4$, $R^5$ and $R^6$ contain collectively at least nine carbon atoms;

to react with an alkylating agent, $R^3X$, wherein $R^3$ is methyl or ethyl; and X is halo, alkyl sulfate or alkyl sulfonate.

9. The composition of claim 8 in which $R^4$, $R^5$ and $R^6$ are independently $C_1$–$C_{21}$ alkyl; $R^1$ is $C_1$–$C_{12}$ alkyl; and $R^2$ is methyl or ethyl.

10. The composition of claim 9 in which $R^3$ is methyl and X is iodo.

11. The compound of claim 2 in which $R^4R^5R^6C$— is a mixture of $C_{16}$–$C_{22}$ alkyl groups.

12. The compound of claim 11 in which $R^1$, $R^2$ and $R^3$ are methyl and $X^-$ is halide, phosphonate or a chelating carboxylic acid.

13. The compound of claim 12 in which $X^-$ is bromide or iodide.

14. The compound of claim 2 in which $R^1$ is n-$C_{12}$ alkyl and $R^4R^5R^6C$— is a mixture of $C_{10}$–$C_{15}$ alkyl groups.

15. The compound of claim 14 in which $R^2$ and $R^3$ are methyl and $X^-$ is halide, phosphonate or a chelating carboxylic acid.

16. The compound of claim 15 in which $X^-$ is bromide or iodide.

* * * * *